(12) United States Patent
Gorsuch et al.

(10) Patent No.: US 6,659,973 B2
(45) Date of Patent: Dec. 9, 2003

(54) APPARATUS AND METHOD FOR IN-VIVO PLASMAPHERESIS USING PERIODIC BACKFLUSH

(75) Inventors: Reynolds G. Gorsuch, Yountville, CA (US); Tommy Cooper, Friendswood, TX (US)

(73) Assignee: Transvivo, Inc., Napa, CA (US)

( * ) Notice: Subject to any disclaimer, the term of this patent is extended or adjusted under 35 U.S.C. 154(b) by 182 days.

(21) Appl. No.: 09/754,773

(22) Filed: Jan. 4, 2001

(65) Prior Publication Data

US 2002/0087109 A1 Jul. 4, 2002

(51) Int. Cl.[7] .............................................. A61M 37/00
(52) U.S. Cl. ................... 604/6.04; 604/6.09; 604/6.11; 604/6.01; 604/5.01; 604/4.01
(58) Field of Search ............................... 604/6.11, 6.09, 604/6.01, 5.01, 4.01, 5.04, 28, 29; 607/6

(56) References Cited

U.S. PATENT DOCUMENTS

| | | | |
|---|---|---|---|
| 4,086,924 A | * 5/1978 | Latham, Jr. ............. 128/214 R |
| 4,235,231 A | 11/1980 | Schindler et al. ........... 128/214 |
| 4,668,214 A | * 5/1987 | Reeder ......................... 494/37 |
| 4,708,799 A | * 11/1987 | Gerlach et al. ........ 210/500.23 |
| 4,832,034 A | 5/1989 | Pizziconi et al. ........... 128/632 |
| 4,919,817 A | * 4/1990 | Schoendorfer et al. ..... 210/639 |
| 4,950,224 A | 8/1990 | Gorsuch et al. ................ 604/4 |
| 5,053,121 A | * 10/1991 | Schoendorfer et al. ....... 210/90 |
| 5,145,583 A | 9/1992 | Angleraud et al. ......... 210/646 |
| 5,151,082 A | 9/1992 | Gorsuch et al. ................ 604/4 |
| 5,152,743 A | 10/1992 | Gorsuch et al. ................ 604/4 |
| 5,211,850 A | * 5/1993 | Shettigar et al. ............ 210/645 |
| 5,224,926 A | 7/1993 | Gorsuch et al. ................ 604/4 |
| 5,242,382 A | 9/1993 | Gorsuch et al. ................ 604/4 |
| 5,536,412 A | * 7/1996 | Ash ........................... 210/645 |
| 5,549,674 A | * 8/1996 | Humes et al. ................ 623/11 |
| 5,674,452 A | * 10/1997 | Carson et al. ................ 422/46 |
| 5,735,809 A | * 4/1998 | Gorsuch ........................ 604/4 |
| 5,868,717 A | * 2/1999 | Prost .......................... 604/264 |
| 5,968,004 A | 10/1999 | Gorsuch ........................ 604/4 |
| 5,980,481 A | * 11/1999 | Gorsuch ....................... 604/28 |
| 6,044,691 A | * 4/2000 | Kenley et al. ........... 73/40.5 R |

* cited by examiner

Primary Examiner—Ira S. Lazarus
Assistant Examiner—Tu Cam Nguyen
(74) Attorney, Agent, or Firm—Knobbe, Martens, Olson & Bear, LLP

(57) ABSTRACT

Apparatus and method for in-vivo plasmapheresis utilizing a plurality of elongated hollow microporous filter fibers periodically interrupt diffusion of blood plasma from a patient, and, for a selected time, backflush fluid into the fibers at a pressure and interval sufficient to cleanse the fiber pores, after which plasma diffusion is resumed.

39 Claims, 3 Drawing Sheets

APPARATUS AND METHOD FOR IN-VIVO PLASMAPHERESIS USING PERIODIC BACKFLUSH

BACKGROUND OF THE INVENTION

In U.S. Pat. Nos. 4,950,224, 5,152,743, 5,151,082, 5,735,809 and 5,980,481 there are disclosed methods and apparatus for carrying out in-vivo plasmapheresis for separating plasma from other blood components within the body and blood vessels of a patient. In the apparatus pumping is used to create a trans-membrane pressure and motivate the flow of fluid from within the in-vivo system, whereby blood plasma is pumped from the patient to a treatment system such as a dialyzer or other apparatus in which toxic metabolic waste in the plasma is removed. After the plasma is treated for removal of waste products, excess fluids, toxins, and/or other deleterious plasma proteins, the treated plasma is returned and reintroduced to the patient's blood stream. Methods of toxin removal from blood, as taught by the aforesaid patents and referred to as plasma dialysis, ultra-filtration or blood purification, are unique from and substantially superior to conventional hemodialysis as presently practiced for both acute and chronic kidney failure, primarily because removal of whole blood from the patient's vasculature is eliminated from the procedure using plasma, or portions of the plasma. The methods and apparatus described in the aforesaid patents are incorporated herein by reference.

In U.S. Pat. Nos. 5,224,926, 5,735,809 and 5,968,004 there are disclosed improved filter assemblies including elongated hollow fibers and various filter assembly designs incorporating such hollow fibers to be used in the above-described methods and apparatus. In U.S. patent application Ser. No. 09/549,131, filed Apr. 13, 2000 (TRANSVI.007), there is disclosed specialized hollow fiber membranes which are superior in biocompatibility, performance and morphology for use in the aforesaid in-vivo plasmapheresis. Such fibers and filter assembly designs, as disclosed in the aforesaid patents and application, are incorporated herein by reference.

In the aforesaid systems, the hollow fiber membranes function as filters, where the primary purpose of said membranes is separation of specific blood or plasma components from whole blood. In such systems, the blood (permeate) flows on the outside of the fiber and the plasma (exudate) is diffused through the fiber membrane to the interior lumen of the hollow fiber. However, as use is continued, performance of the fibers as filters becomes degraded over time. For example, clogging or fouling of the filter occurs on the surface of the filter as the pore void spaces become more occluded with particulate matter from the permeate building up within the pore void such that the minute volume of the exudate is progressively degraded to the point of failure and cessation of exudate flow. Such clogging or fouling of the filter membranes, as well as clotting problems with prior art filter systems as disclosed in the aforesaid application Ser. No. 09/549,131 (TRANSVI.007), causes major operational and economic problems with current ex-vivo systems performing Continuous Renal Replacement Therapy (CRRT) for acute and chronic kidney failure. It is reported by Ramesh, Prasad, et al., in *Clinical Neprology*, Vol. 53, p. 55–60 (January 2000), that over 50% of such filters fail in 10 hours and over 75% fail in 30 hours of usage. Because short-term filter replacement is both undesirable and unacceptable, clogging or fouling failure of filters used in in-vivo systems described in the aforesaid patents would be totally unacceptable for both medical and economic reasons.

SUMMARY OF THE INVENTION

According to the present invention, in-vivo plasmapheresis is periodically interrupted and a backflush fluid is directed into the interior of the hollow fibers of the filter device for a duration and at a flow rate sufficient to substantially cleanse the pores of the filter. After a sufficient duration, the backflush is terminated and the plasmapheresis extraction is resumed. The apparatus for carrying out the improvement of the invention includes a multiple lumen catheter having a first lumen for directing backflush fluid into the hollow fibers, a second fluid for directing plasma from the filter assembly, and a third lumen for returning treated plasma to the patient. The apparatus also includes one or more pumps for pumping the backflush fluid into the filter assembly.

DETAILED DESCRIPTION OF THE PREFERRED EMBODIMENT

Figure 1:
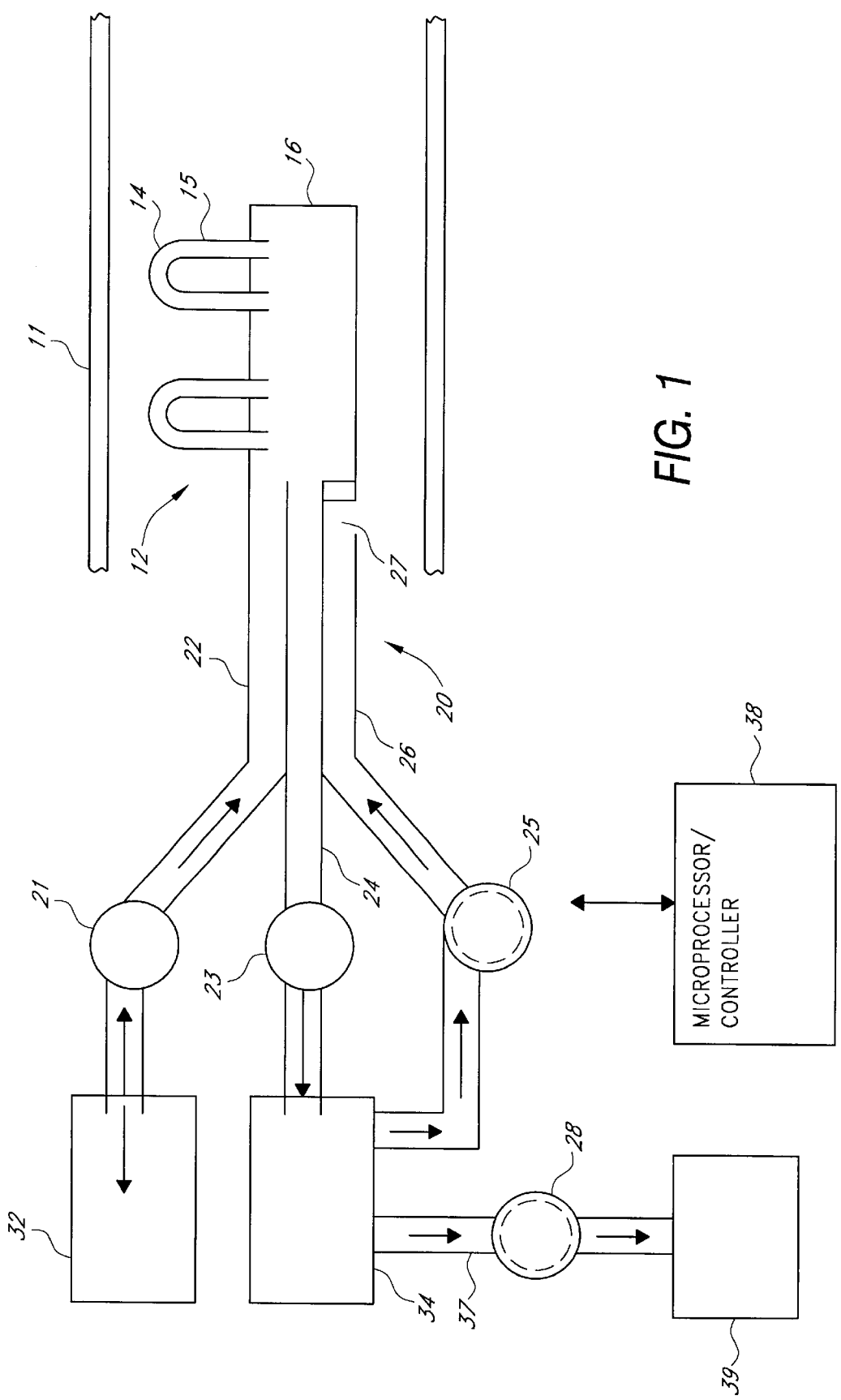
FIG. 1 is a schematic illustration of an apparatus for carrying out the improved method of the invention.

As illustrated in FIG. 1, the apparatus for carrying out the invention comprises a filter assembly 12 having a plurality of hollow fiber membranes 14. The terminal ends of the fibers are potted into an extraction header 16 which provides fluid communication between the hollow interior 15 of each of the fiber membranes and into the interior lumens of the triple-lumen catheter 20. The catheter 20 comprises a first lumen 22 for directing backflush fluid through the header 16 into the hollow interior of the elongated fiber membranes. A second lumen 24 directs plasma from the filter assembly to a plasma treatment apparatus 34 to provide ultrafiltration, dialysis, replacement, column adsorption, or a bioreactor or other such apparatus for treating or utilizing the plasma. A third lumen 26 directs the treated plasma back to the patient. Providing a separate lumen (22) for backflush fluid instead of using exudate lumen (24) for backflush eliminates dead-space in lumen 24 and the necessity of removing and reintroducing exudate to accommodate such backflush. The apparatus also includes one or more positive displacement pumps. A first pump 21 pumps fluid from a source of backflush fluid 32 at predetermined intervals and for a predetermined and selected duration as will be explained further hereinafter. A second positive displacement pump 23 pumps plasma exudate from the filter assembly via catheter lumen 24 through the treatment apparatus 34 and back to the patient via third catheter lumen 26. In other selected systems a third positive displacement pump 25 is used to pump the treated plasma or plasma component back to the patient via third catheter lumen 26. The catheter includes an orifice 27 which directs the returned treated plasma into the patient's blood vessel 11.

The apparatus may also provide means for collecting and disposing of plasma components such as toxins, excess plasma water, etc, separated in the plasma exudate in treatment apparatus 34, and which are not to be returned to the patient. Such means is connected to the plasma treatment apparatus via conduit 37 and includes a collection container 39 and a pump 28 for pumping the effluent to be removed from the plasma exudate to the container.

Figure 2:
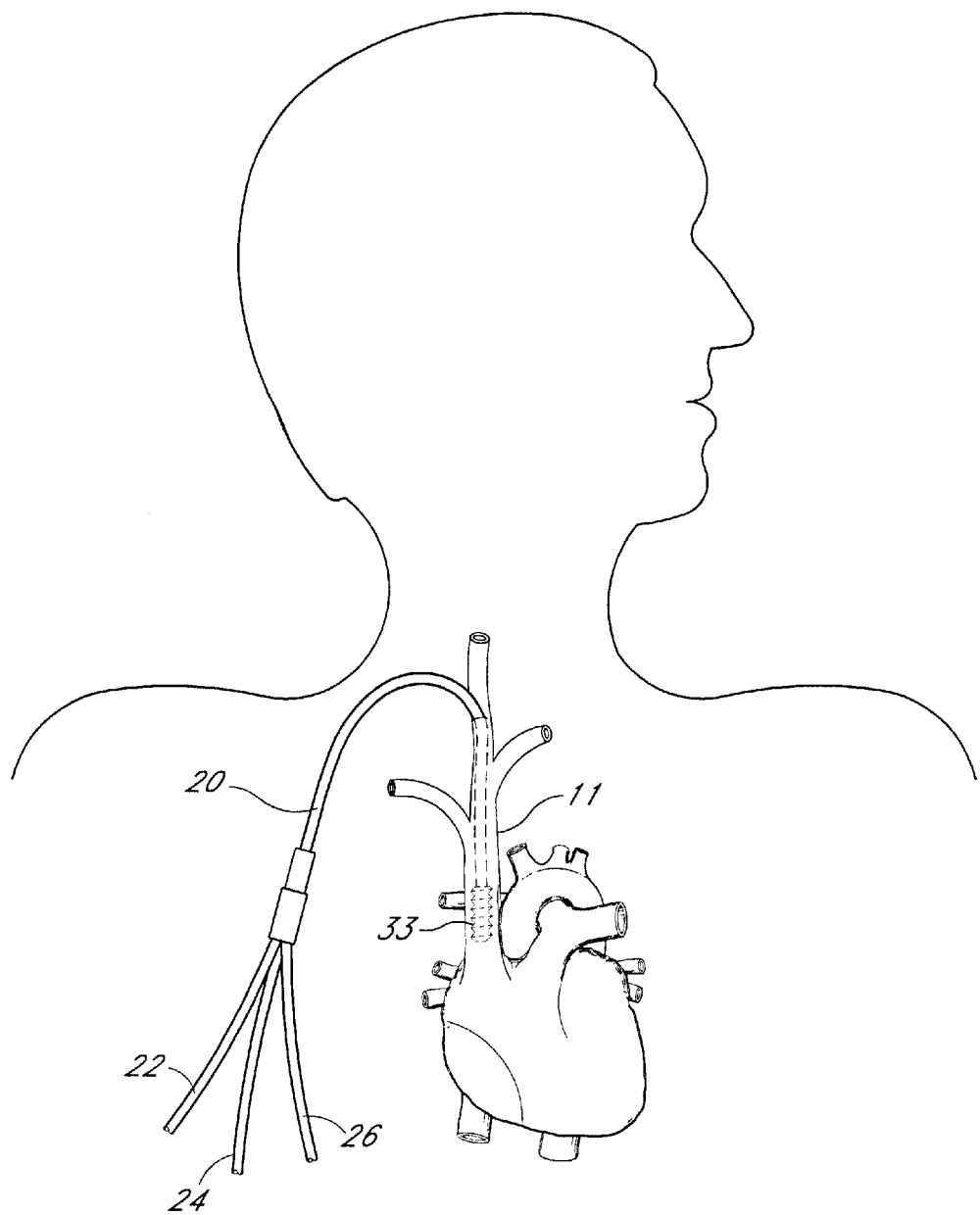
FIG. 2 illustrates an apparatus of the invention implanted in a patient.

The filter assembly 12, including the header and elongated hollow microporous membrane fibers 14, is implanted in a blood vessel 11 of the patient, preferably the vena cava, or other suitable blood vessel as described in the aforesaid patents. A preferred fiber membrane used in the filter assembly is disclosed in aforesaid application Ser. No. 09/549,131. Such a membrane has a plurality of zones between the inner and outer wall surfaces, each zone having a different mass density than the mass density of an adjacent zone. The membrane fiber wall may have two, three or four or more mass density zones with a lower mass density zone at the inner wall surface and a higher mass density zone at the outer wall surface. Each zone is characterized by a different average moninal pore size, with a lower mass density zone having a nominal average pore size of between about 1 um and about 60 um and a higher mass density zone having a nominal average pore diameter of between about 0.3 um and about 1 um. A preferred membrane has the capability of extracting at least 0.75 (ml/min)/(cm$^2$×mmHg) at transmembrane pressures of between about 5 mm and about 20 mmHG. Preferred fibers have a sieving coefficient cutoff of between $2 \times 10^4$ and $4 \times 10^6$ Daltons. An implanted filter assembly is illustrated in FIG. 2 and further described in the aforesaid patents.

The backflush fluid source 32 comprises a container, bag or other suitable source of a backflush fluid, for example, a normal saline solution, or a source of fresh or treated plasma from which toxins, high molecular weight proteins and/or other undesirable contaminants have been removed. The apparatus also includes a microprocessor/controller 38 which controls operation of the pumps and manages the system. The microprocessor/controller is calibrated to determine the flowrate of the pumps. The system may include one or more pressure transducers for monitoring the pressure of fluids within all lumens. Such transducers, not shown, may be used to measure the transmembrane pressure thereby indicating when the pores of the filter have become clogged to an extent to terminate the extraction period, and initiate the backflush operation of the apparatus. Depending on the exudate flow determined by the microprocessor/controller and the transmembrane pressure sensed by such transducers, the microprocessor/controller may determine the duration of the backflush period, as well as the backflush flow rate to be used for substantially cleansing the pores of the fiber membrane. Pumps may also be provided having variable pressure capabilities which may also be regulated by the microprocessor/controller, if desired. The microprocessor/controller 38 may be used to manage the system through monitoring of the flows in the lumens of the catheter, particularly the flow of the exudate through catheter 24 and the pumping of the backflush fluid through the catheter lumen 22. Pump 25 may also be operated by the microprocessor/controller for returning the desired amount of treated plasma to the patient.

The backflush cycle is periodic and preferably provided at a high transmembrane pressure and low volume, i.e., a low multiple of the volume contained in the membrane lumens of the hollow fibers of the filter and the extraction header. The combination of high pressure and relatively short injection times for backflushing both expands the membrane pores and dislodges adhered proteins, thereby restoring pore integrity and density of the virtual filter area to an improved performance level after each backflush cycle. Thus, the process of the invention not only prevents degradation due to clogging, but over time improves the yield of transmembrane exudate flux in terms of (ml/min)/(cm$^2$×mmHg) by progressively adjusting and thus optimizing the backflush parameters. Backflush pressures used are between about 15 and about 100 mmHg which are substantially less than the trans-membrane pressure which is deemed safe since the burst pressures of the membranes are greater than 760 mmHg.

As previously noted, the pumps used in the apparatus of the invention are positive displacement roller pumps. Thus, the fluid flows for both exudate extraction via catheter lumen 24 and backflush fluid injection via catheter lumen 22 are functions of the diameter of the tubing used and the pump revolutions per second. The microprocessor/controller is calibrated to the parameters of the tubing diameter and pump revolutions, thereby equating fluid volume pumped to the time of operation. For example, the setting of the parameters for the control and regulation of the pumps may be empirically determined for equating the volume and time for exudate extraction and backflush injection functions of the apparatus. By way of example, such parameters found to be useful for plasmapheresis have been empirically determined for an exudate extraction period of between about 240 and about 600 sec, and a backflush duration of between about 5 and about 50 sec, thereby yielding a preferred backflush fluid flow of between 5 and 45 ml/min. The settings for such parameters are determined by catheter design and by blood flow conditions around the filter and plasma extraction membrane. Again, it is desired and preferred to deliver a minimum amount of saline backflush fluid for cleansing the hollow fiber membrane pores. Moreover, the volume of the backflush injection bolus must be greater than the dead space volume of the catheter extraction header, the inner lumen of the hollow fibers, and the interstitial space in the membrane walls. In addition to the dead space volume, a certain amount of saline is needed to wash out the material that fouls the membrane. The volume of this washing fluid is dependent upon the surface area of the membrane and may be expressed as a bolus flux in ml/cm$^2$. By way of example, a bolus flux used for in-vivo and in-vitro tests is 0.03 ml/cm$^2$. Again, the injection bolus volume is determined from the dead space volume and the membrane surface areas set by the catheter design.

The time between backflush periods may be determined by how quickly the membrane becomes clogged. Unnecessarily short intervals between backflushes results in higher average backflush flow rates, thereby reducing the amount of plasma removed. On the other hand, where backflush intervals are overly long, plasma flow rates decline due to filter fouling. For example, an empirically determined interval between backflushes of 300 sec has been found to be useful for existing catheter designs.

The flow rate for backflush fluid injections is determined by pressure limitations of the catheter, the effect of flow velocity for substantially cleansing or clearing the membrane, and the amount of backflush or bolus volume required. A rise in pressure is a result of resistance to flow due to clogged membranes and is a function of the backflush flow rate, membrane surface area, and level of membrane clogging. The flow rate is also limited by the amount of pressure that the inner lumen of the catheter and fibers can withstand without failure. As previously noted, the velocity or pressure of the backflush fluid must be sufficient to dislodge the clogging material in all of the membrane surface. It has been found that with 16 ml/min and a surface area of 40 cm$^2$, by using a backflush pressure of 15 mmHg, all of the membrane is sufficiently and substantially cleared. The duration of the backflush bolus may also be lengthened or shortened to adjust the backflush flow volume. While the period between backflush intervals and the flow rate are closely related to membrane clearing requirements, the duration is not, thereby making it an obvious choice for adjustment of bolus volume. For example, a catheter with a dead volume of 1.5 ml and a surface area of 40 cm$^2$ requires a bolus volume of 2.7 ml. A plasma extraction period of 300 sec and a flow rate of 16 ml/min results in a backflush duration of about 10 sec. The average backflush flow rate is computed to be 0.54 ml/min.

The clogging or fouling of the filtration membrane is a function of the flow rate of exudate through the extraction filter assembly, the size of which, i.e., cm$^2$ of membrane surface area, is dictated by the clinical application to be served. Generally, the more advanced disease state of organ failure to be served requires greater exudate flow rate and a greater membrane surface area, resulting in earlier degradation of extraction performance and requiring a more aggressive program for backflush cleansing of the membrane. Thus, for example, treatment of advanced acute renal failure (ARF) and end stage renal disease (ESRD) requires substantially higher fluid extraction rates for optimum clinical results as compared to fluid management systems for treating congestive heart failure (CHF).

Figure 3:
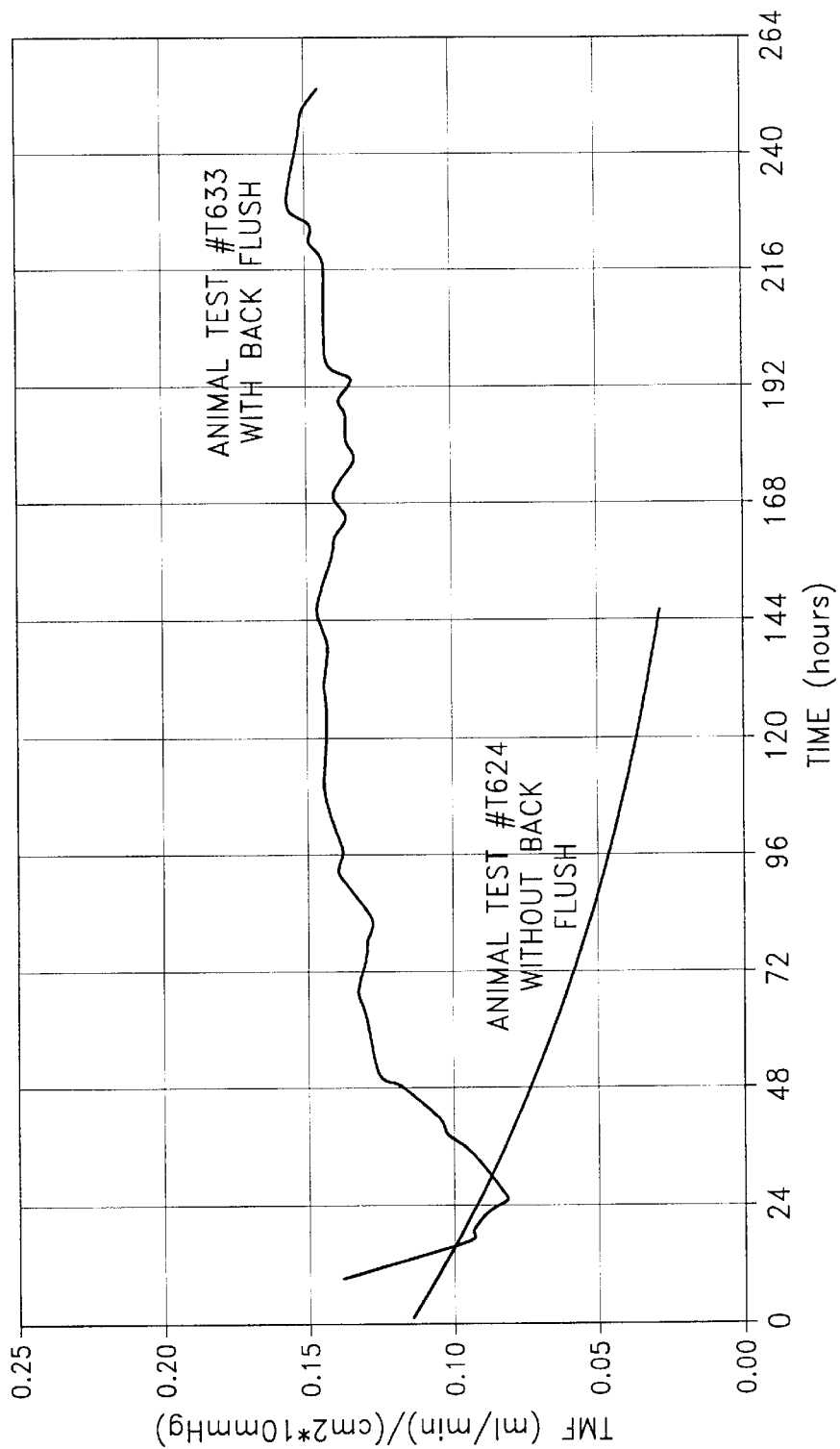
FIG. 3 is a graph illustrating trans-membrane flux degradation trends with and without periodic backflush of the invention.

A comparison of a system using backflush components and methods of the invention with a system having no backflush is illustrated in the graph of FIG. 3, and based on actual test results which have been repeated over time. The results show marked improvement using apparatus and method of the invention.

Medical applications of systems using the aforesaid invention include fluid management for patients in decompensated congestive heart failure and prevention of pre-renal kidney failure and acute respiratory distress syndrome, treatment of refractive congestive heart failure and acute renal failure, as well as therapeutic apheresis systems for immune system disease and blood component therapy, edema, management systems for ascites, lymphedema, and selective systemic edema, tissue engineering applications including bioreactors and hybrid bio-organs, and dialysis systems for end stage renal disease. Other uses and applications will be appreciated by those skilled in the art.

What is claimed is:

1. Apparatus for carrying out in-vivo plasmapheresis comprising:
    a filter assembly for being implanted in a blood vessel comprising a plurality of elongated hollow microporous membrane fibers for diffusing plasma therethrough and a header in fluid communication with the interior of said hollow fibers;
    a multiple lumen catheter in fluid communication with said header comprising a first lumen in fluid communication with the interior of said fibers for directing backflush fluid through said header into the interior of said hollow fibers, a second lumen in fluid communication with the interior of said fibers for directing plasma from said filter assembly, and a third lumen for returning plasma to the blood vessel; and
    a pump in fluid communication with said first lumen for periodically pumping backflush fluid into the interior of said fibers and through the membrane thereof.

2. Apparatus of claim 1 including a source of backflush fluid in fluid communication with said pump and said first lumen.

3. Apparatus of claim 1 including a microprocessor/controller operatively connected to said pump.

4. Apparatus of claim 3 wherein said microprocessor/controller and said pump cooperate to direct said backflush fluid into said microporous membrane fibers for a duration and at a flow rate sufficient to backflush and substantially cleanse the membrane pores.

5. Apparatus of claim 4 wherein said microprocessor/controller and said pump cooperate to direct said backflush fluid into said microporous membrane fibers at a pressure sufficient to substantially cleanse the membrane pores.

6. Apparatus of claim 1 wherein said pump in fluid communication with said first lumen is a first pump, said apparatus including a second pump in fluid communication with said second lumen for pumping plasma from said filter to plasma treatment apparatus.

7. Apparatus of claim 6 including a third pump in fluid communication with said third lumen for pumping plasma from plasma treatment apparatus to the blood vessel.

8. Apparatus of claim 7 including a microprocessor/controller operatively connected to said first, second and third pumps.

9. Apparatus of claim 8 wherein said microprocessor/controller and said first pump cooperate to direct said backflush fluid into said microporous membrane fibers for a duration and at a flow rate sufficient to backflush and substantially cleanse the membrane pores.

10. Apparatus of claim 9 wherein said microprocessor/controller and said first pump cooperate to direct said backflush fluid into said microporous membrane fibers at a pressure sufficient to substantially cleanse the membrane pores.

11. Apparatus of claim 6, 7, 8 or 9 including a pump and conduit cooperating therewith for pumping separated plasma components from plasma treatment apparatus to a container.

12. Apparatus for carrying out in-vivo plasmapheresis comprising:
    a filter for being planted in a patient's blood vessel comprising a plurality of elongated hollow microporous fibers having an interior lumen and a fiber wall having a pore size capable of allowing plasma to diffuse therethrough;
    a multiple lumen catheter in fluid communication with the interior fiber lumen including a first lumen for directing backflush fluid into said fiber lumen and a second lumen for directing plasma from said fiber lumen; and
    means for periodically pumping backflush fluid into said first fiber lumen at a pressure and duration sufficient to backflush and cleanse the pores of the fiber walls.

13. Apparatus of claim 12 wherein said means for pumping backflush fluid comprise one or more positive displacement pumps cooperating with said catheter.

14. Apparatus of claim 12 wherein said one or more pumps is capable of pumping the backflush fluid at a pressure of between about 15 and about 100 mg Hg for a duration of between about 5 and about 50 seconds.

15. Apparatus of claim 13 wherein said one or more pumps is capable of pumping said backflush fluid at a rate of between about 5 and about 45 ml/minute.

16. Apparatus of claim 12, 13, 14 or 15 wherein said catheter includes a third lumen for returning plasma to the patient's blood vessel.

17. Apparatus of claim 1 or 12 wherein said fibers have a sieving coefficient cutoff of between $2 \times 10^4$ and $4 \times 10^6$ Daltons.

18. Apparatus of claim 1 or 12 wherein said fibers comprise a fiber wall having a plurality of zones between the inner and outer wall surfaces, each of said zones having a mass density different than the mass density of an adjacent zone, said fiber wall characterized by having a lower mass density zone at the inner wall surface and a higher mass density zone at the outer wall surface.

19. A membrane of claim 18 wherein said membrane fiber wall has two mass density zones.

20. A membrane of claim 18 wherein said membrane fiber wall has three mass density zones.

21. A membrane of claim 18 wherein membrane fiber wall has four or more mass density zones.

22. A membrane of claim 18 wherein each of said zones is characterized by a different average nominal pore size.

23. A membrane of claim 22 capable of in-vivo plasmapheresis wherein said lower mass density zone is characterized by a nominal average pore diameter of between about 1 μm and about 60 μm.

24. A membrane of claim 22 wherein said higher mass density zone is characterized by a nominal average pore diameter of between about 0.3 μm and about 1 μm.

25. A membrane of claim 23 wherein said higher mass density zone is characterized by a nominal average pore diameter of between about 0.3 μm and about 1 μm.

26. A membrane of claim 18 characterized by having the capability of extracting at least 0.75 (ml/min)(cm$^2$×mmHg) of blood plasma at trans-membrane pressures of between about 5 and about 20 mmHg.

27. Apparatus of claim 12 wherein said means for pumping backflush fluid is one or more first pumps cooperating with said first lumen for pumping said backflush fluid therethrough, and wherein said apparatus includes one or more second pumps cooperating with said second lumen for pumping plasma from said fibers therethrough.

28. Apparatus of claim 27 including one or more third pumps cooperating with said third lumen for pumping plasma therethrough.

29. Apparatus of claim 28 including plasma treatment apparatus for removing toxins from the plasma diffused through the fibers.

30. Apparatus of claim 29 including a pump and conduit cooperating therewith for pumping separated plasma components from plasma treatment apparatus to a container.

31. A method of carrying out in-vivo plasmapheresis comprising:

implanting a filter device within a blood vessel of a patient, said filter device comprising a plurality of elongated hollow microporous fibers;

providing a multiple lumen catheter in fluid communication with the hollow interior of said fibers; and diffusing plasma and toxins from the patient's blood through the wall of said fibers into the hollow interior thereof, and therefrom through a second lumen of said catheter;

periodically interrupting said diffusion of plasma and toxins and thereafter directing a fluid through a first lumen of said catheter into said fibers and backflushing said fibers with said fluid at a pressure and for an interval sufficient to substantially cleanse the pores of said filter, and after said interval, resuming said diffusion of plasma.

32. A method of claim 31 wherein the fluid is backflushed at a pressure of between about 15 and about 100 mg Hg for an interval of between about 5 and about 50 seconds.

33. A method of claim 31 or 32 wherein said backflush fluid comprises saline solution.

34. A method of claim 31 or 32 wherein said fluid is backflushed by pumping said fluid into the hollow interior of said fibers.

35. A method of claim 34 wherein said fluid is pumped into said fibers at a pressure of between about 15 and about 100 mg Hg.

36. A method of claim 34 wherein said fluid is pumped into said fiber for an interval of between about 5 and about 50 seconds.

37. A method of claim 31 including a plasma treatment apparatus, and wherein toxin-containing plasma from said fibers is directed to said plasma treatment apparatus through said second lumen of said catheter.

38. A method of claim 37 wherein plasma from said plasma treatment apparatus is directed to a third lumen of said catheter and returned to said patient.

39. A method of claim 35 wherein said fluid is pumped into said fiber for an interval of between about 5 and about 50 seconds.

* * * * *